United States Patent [19]

Khanna et al.

[11] Patent Number: 5,159,071
[45] Date of Patent: Oct. 27, 1992

[54] PROCESS FOR THE MANUFACTURE OF 7-AMINO-3-EXOMETHYLENE-3-CEPHAM-4-CARBOXYLIC ACID ESTER

[75] Inventors: Jag M. Khanna; Yatendra Kumar; Mashkoor Husain, all of New Delhi, India

[73] Assignee: Ranbaxy Laboratories Limited, New Delhi, India

[21] Appl. No.: 696,099

[22] Filed: May 6, 1991

[30] Foreign Application Priority Data

Sep. 6, 1990 [IN] India .............. 893/DEL/90

[51] Int. Cl.$^5$ .......................................... C07D 501/04
[52] U.S. Cl. ...................................... 540/215; 540/230
[58] Field of Search ................ 540/215, 230, 222, 221

[56] References Cited

U.S. PATENT DOCUMENTS

| | | | |
|---|---|---|---|
| 3,896,118 | 7/1975 | Ishimaru et al. | 540/219 |
| 3,925,372 | 12/1975 | Chauvette | 260/243 C |
| 4,044,002 | 8/1977 | Hatfield | 544/16 |
| 4,115,643 | 9/1978 | Kukolja et al. | 544/16 |
| 4,223,133 | 9/1980 | Bunnell | 544/16 |
| 4,252,973 | 2/1981 | Slusarchyk et al. | 544/21 |
| 4,695,627 | 9/1987 | Verweij et al. | 540/224 |
| 4,950,753 | 8/1990 | Copp et al. | 540/215 |
| 5,109,132 | 4/1992 | Verweij et al. | 540/215 |

OTHER PUBLICATIONS

M. Ochiai et al., "Reactions and Determination of Stereochemistry of 3-Methylenecepham Derivatives," Tetrahedron Letters No. 31, pp. 3241–3244, 1972, Pergamon Press.

M. Ochia et al., "Electrochemical Reduction of Cephalosporanic Acids. A New Synthesis of 7-(-D-2-Amino-2-Phenylacetamido)-3-Desacetoxycephalosporanic Acid" Tetrahedron Letters No. 23, pp. 2341–2344, 1972, Pergamon Press.

R. Chauvette et al., J. Org. Chem. vol. 138, No. 17, 1973, pp. 2994–2999.

*Primary Examiner*—Nicholas S. Rizzo
*Attorney, Agent, or Firm*—Marmorek, Guttman & Rubenstein

[57] ABSTRACT

A one-pot process for preparing 7-amino-3-exomethylene-3-cepham-4-carboxylic acid ester (II) comprises: (a) reacting 7-acylamino-3-exomethylene-3-cepham-1-oxide-4-carboxylic acid ester (I) with a silylating agent in an inert solvent and in the presence of a base, (b) adding a phosphorous halide to produce an iminohalide, and (c) adding an anhydrous alcohol. In a preferred embodiment, the silylating agent comprises trimethylchlorosilane, and the phosphorous halide comprises phosphorous pentachloride.

24 Claims, No Drawings

PROCESS FOR THE MANUFACTURE OF 7-AMINO-3-EXOMETHYLENE-3-CEPHAM-4-CARBOXYLIC ACID ESTER

BACKGROUND OF THE INVENTION

The present invention relates to a novel one-pot process for the preparation of 7-amino-3-exomethylene-3-cepham-4-carboxylic acid ester hydrochloride (II) by deoxygenation and deacylation of the side chain of 7-acylamino-3-exomethylene-3-cepham-1-oxide-4-carboxylic acid ester (I).

7-acylamino-3-exomethylene-3-cepham-1-oxide-4-carboxylic acid ester (I) and 7-amino-3-exomethylene-3-cepham-4-carboxylic acid ester hydrochloride (II) are important intermediates in some reaction schemes for the manufacture of clinically useful antibacterial agents, such as Cefaclor (7-D-phenylglycylamido-3-chloro-3-cephem-4-carboxylic acid).

A previously known method, for converting 7-acylamino-3-exomethylene-3-cepham-1-oxide-4-carboxylic acid ester (I) into 7-amino-3-exomethylene-3-cepham-4-carboxylic acid ester (II) requires two steps and the overall yield is low. These steps are: 1) deoxygenation of 3-exomethylene sulfoxide (I) by treatment with phosphorous trichloride in DMF [see ref.: "Recent Advances in Chemistry of Beta-lactam Antibiotics," special publication No. 28, page 107 (1976)], and 2) deacylation by treating the isolated sulphide (III) with phosphorous pentachloride and pyridine followed by the addition of anhydrous alcohol (methanol, isobutanol, etc.) to give the desired 7-amino-3-exomethylene (II) [see ref.: *J. Org. Chem.*, 38, 2995 (1973)].

The prior art two-step reaction scheme is illustrated below showing the production and isolation of the intermediate sulphide (III):

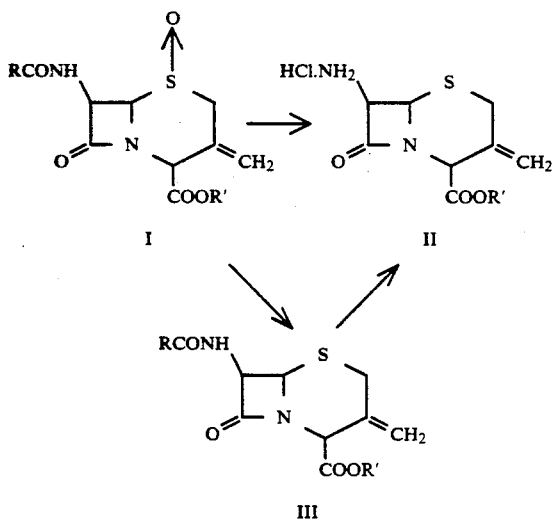

SUMMARY AND DETAILED DESCRIPTION OF THE INVENTION

According to the process of this invention, 7-amino-3-exomethylene-3-cepham-4-carboxylic acid ester having the general formula II can be manufactured in a one-pot process, without the production and isolation of the intermediate sulphide (III), by (a) reacting 7-acylamino-3-exomethylene-3-cepham-1-oxide-4-carboxylic acid ester having the general formula I with a silylating agent in an inert solvent and in the presence of a base, (b) adding a phosphorous halide to form an iminohalide, (c) followed by the addition of an anhydrous alcohol. 7-amino-3-exomethylene-3-cepham-4-carboxylic acid ester (II) separates out as a hydrochloride from the reaction mixture. Step (a) is carried out at a temperature of about 0° to about 50° C., preferably at about 10° to about 20° C.; step (b) is carried out at a temperature of about −50° to about +20° C., preferably at about −30° C. to about −20° C.; step (c) is carried out at a temperature of about −50° to about +30° C., preferably at about −30° to about +20° C. The silylating agent activates the amido group by forming O-silyl derivative in the presence of base, which derivative is converted into the iminohalide by the addition of phosphorous halide. If the silylating reagent is not added prior to the addition of phosphorous halide, the yields are very low.

In the above formulas, R' stands for linear or branched alkyl, aryl, aralkyl, aryloxyalkyl, alkoxylalkyl and the like. Highly preferred substituents are p-nitrobenzyl, p-methoxybenzyl, and benzhydryl. R stands for aryl, aralkyl, aryloxyalkyl, and the like. Highly preferred substituents are benzyl and phenoxyethyl.

Suitable silylating agents are, preferably, strong silylating reagents such as trimethyl chlorosilane, dimethyl dichlorosilane, methyltrichlorosilane, triethylchlorosilane, trimethylbromosilane, methoxytrichlorosilane, N,O-bistrimethylsilylacetamide, and the like. Trimethylchlorosilane (TMCS) and dimethyl dichlorosilane are most preferred.

The bases used in accordance with the invention are preferably organic bases, especially N,N-dialkylanilines such as N,N-dimethyl aniline, N,N-diethyl aniline and triethyl amine, pyridine, etc. N,N-dimethyl aniline is especially suitable for the process of the invention.

Phosphorous halides used as iminohalide forming agents in the process of this invention are phosphorous pentachloride, phosphorous pentabromide, phosphorous trichloride, phosphorous tribromide, and the like. Phosphorous pentachloride is most preferred.

Anhydrous alcohols used in the process of this invention are methanol, ethanol, isobutanol, n-propanol, isopropanol, ethylene glycol, 1,3-propanediol, propylene glycol and the like. Preferred examples of alcohols include methanol, isobutanol and 1,3-propanediol.

Inert organic solvents used in the process of this invention are methylene chloride, chloroform, ethylene chloride, propylene chloride, carbon tetrachloride, trichloroethane and the like. Preferred examples are methylene chloride, chloroform and carbon tetrachloride.

The invention will now be described by reference to the following examples.

EXAMPLE 1

7-Amino-3-exomethylene-3-cepham-4-carboxylic acid-p-nitrobenzyl ester hydrochloride To a solution of 7-phenoxyacetamido-3-exomethylene-3-cepham-1-oxide-4-carboxylic acid p-nitrobenzyl ester (100 g, 0.20 mole) in methylene chloride (1L) were added TMCS (56.2 mL, 0.44 mole) and N,N-dimethylaniline (75.7 mL, 0.6 mole) at 15°-20° C. The reaction mixture was stirred for 1 hr. and then cooled to −40° C. PCl$_5$ (91.7 g, 0.44 mole) was added and the reaction mixture was further stirred for 2.5 hrs. at −30° C. Again it was cooled to −50° C. and isobutanol (100 mL, 1.10 mole) was added. The temp. of the mixture went up to −30° C. during the addition. The solution was stirred for 15 min. at −30° C. and for 2 hrs. at 0° C. During the stirring, the solid separated out, which was filtered and thoroughly washed with methylene chloride and dried.

Yield 64 g (83%); m.p. 182°–83° C. (dec.); IR (KBr): 1770, 1740, 1610, 1525, 1500, 1350, 1175, 845, 735 cm$^{-1}$.

NMR (DMSO-d$_6$): δ3.6(dd, 2H, C$_2$—CH$_2$), 4.7 (d, 1H, C$_6$—CH), 4.8–5.3 (m, 6H, C$_4$—CH, ester CH$_2$, C$_3$—CH$_2$ and C$_7$—CH), 7.2–8.0 (m, 4H, Ar-H)

Anal: for C$_{15}$H$_{16}$N$_3$O$_5$SCl, Clcd; C:46.69. H: 4.18, N:10.89. Found: C:46.70, H:4.25, N:10.75

EXAMPLE 2

7-Amino-3-exomethylene-3-cepham-4-carboxylic acid-p-nitrobenzyl ester hydrochloride To a solution of 7-phenoxyacetamido-3-exomethylene-3-cepham-1-oxide-4-carboxylic acid p-nitrobenzyl ester (10 g, 0.02 mole) in methylene chloride (100 mL) were added TMCS (5.62 mL, 0.044 mole) and N,N-dimethylaniline (7.5 mL, 0.06 mole) at 15°–20° C. The reaction mixture was stirred for 1 hr. and then cooled to −40 ° C. PCl$_5$ (9.17 g, 0.044 mole) was added and the reaction mixture was further stirred for 2.5 hrs. at −30° C. Again it was cooled to −50° C. and methanol (5 mL, 0.123 mole) was added. The temperature of the mixture went up to −30° C. during the addition. The solution was stirred for 1 hr. at −3° C. and for 2 hrs. at 0° C. During the stirring, the solid separated out, which was filtered and thoroughly washed with methylene chloride and dried. Yield 5.87 g (76%), m.p. 181°–83° C. (dec.)

EXAMPLE 3

7-Amino-3-exomethylene-3-cepham-4-carboxylic acid p-nitrobenzyl ester

To a solution of 7-phenoxyacetamido-3-exomethylene-3-cepham-1-oxide-4-carboxylic acid p-nitrobenzyl ester (100 g, 0.20 mole) in methylene chloride (1L) were added TMCS (50.8 mL, 0.40 mole) and N,N-dimethylaniline (63.5 mL, 0.50 mole) at 15°–20° C. The reaction mixture was stirred for 1 hr. and then cooled to −40° C. PCl$_5$ (91.7 g, 0.44 mole) was added and the reaction mixture was further stirred for 2.5 hrs. at −30° C. Again it was cooled to −50° C. and 1,3-propanediol (79.6 mL, 1.10 mole) was added. The solution was stirred for 15 min. at −30° C. and for 2 hrs. at 0° C. During the stirring the solid separated out, which was filtered and thoroughly washed with methylene chloride and dried. Yield 63.2 g (81.8%), m.p.: 182°–83° C. (dec.).

EXAMPLE 4

7-Amino-3-exomethylene-3-cepham-4-carboxylic acid p-nitrobenzyl ester hydrochloride To a solution of 7-phenoxyacetamido-3-exomethylene-3-cepham-1-oxide-4-carboxylic acid p-nitrobenzyl ester (100 g, 0.20 mole) in methylene chloride (1 L) was added, N,N-dimethylaniline (55.8 ml, 0.44 mole) at 15°–20° C. The reaction mixture was cooled to −40° C. PCl$_5$ (91.7 g, 0.44 mole) was added and the reaction mixture was stirred for 2 hrs. at −30° C. The temperature was raised to 20° C. and the reaction mixture was stirred for 2 hrs. Again it was cooled to −50° C. and 1,3-propanediol (79.6 mL, 1.10 mole) was added. The solution was stirred for 15 min. at −30° C. and for 2 hrs. at 0° C. During the stirring, the solid separated out, which was filtered and thoroughly washed with methylene chloride and dried. Yield 35.0 g (45.3%), m.p. 182°–83° C. (dec.)

EXAMPLE 5

7-Amino-3-exomethylene-3-cepham-4-carboxylic acid p-nitrobenzyl ester hydrochloride To a solution of 7-phenoxyacetamido-3-exomethylene-3-cepham-1-oxide-4-carboxylic acid p-nitrobenzyl ester (50 g, 0.10 mole) in methylene chloride (500 mL) were added N,N-dimethylaniline (37.8 mL, 0.3 mole) and TMCS (28.1 mL, 0.22 mole) at 15°–20° C. The reaction mixture was stirred for 1 hr. and then cooled to 0° C. PCl$_5$ (45.8 g, 0.22 mole) was added and the reaction mixture was further stirred for 2.5 hrs. at 20° C. Again it was cooled at 0° C. and isobutanol (15 mL, 0.55 mole) was added. The solution was stirred for 15 min. at 0° C. and for 2 hrs. at 20° C. During the stirring the solid separated out, which was filtered, thoroughly washed with methylene chloride and dried. Yield 15.5 g (40%), m.p.: 179°–181° C. (dec.).

EXAMPLE 6

7-Amino-3-exomethylene-3-cepham-4-carboxylic acid p-nitrobenzyl ester hydrochloride To a solution of 7-phenyl-3-exomethylene-3-cepham-1-oxide-4-carboxylic acid p-nitrobenzyl ester (19.30 g, 0.04 mole) in methylene chloride (100 mL) were added TMCS (11.24 mL, 0.088 mole) and N,N-dimethylanilnie (15.14 mL, 0.12 mole) at 15°–20° C. The reaction mixture was stirred for 1 hr. and then cooled to −40° C. PCl$_5$ (18.35 g, 0.088 mole) was added and the reaction mixture was further stirred for 2.5 hrs. at −30° C. Again it was cooled to −50° C. and isobutanol (20 mL, 0.22 mole) was added. The temperature of the mixture went up to −30° C. during the addition. The solution was stirred for 1 hr. at −30° C. and for 2 hrs. at 0° C. During the stirring, the solid separated out, which was filtered and thoroughly washed with methylene chloride and dried. Yield 12.30 g (80%), m.p.: 181°–183° C. (dec.)

EXAMPLE 7

7-Amino-3-exomethylene-3-cepham-4-carboxylic acid diphenyl methyl ester hydrochloride To a solution of 7-phenyl acetamido-3-exomethylene-3-cepham-1-oxide-4-carboxylic acid diphenylmethyl ester (50 g, 0.097 mole) in methylene chloride (500 mL) were added N,N-dimethyl aniline 47 g, 0.388 mole) and TMCS (26 g, 0.24 mole) at 15°–20° C. The reaction mixture was stirred for 1 hr. and then cooled to −40° C. PCl$_5$ (81 g, 0.388 mole) was added and the reaction mixture was further stirred for 2 hrs. at −30° C. The mixture was cooled to −50° C. and methanol (300 mL, 76.5 mole) was added. The solution was stirred for 1 hr. at −15° C. and 1 hr. at 15° C. Water (100 mL) was added and concentrated under vacuum to remove methylene chloride and methanol. The solid thus obtained was filtered, dried. Yield 28 g (70%), mp.: 168°–170° C.

NMR :(DMSO-d$_6$) : 3.4(dd, 2H, C$_2$—CH$_2$), 4.8(d, 1H, c$_6$—CH), 5.1–5.4(m, 4H, C$_7$—CH, C$_4$—CH & C$_3$—CH), 6.6(s, 1H, ester CH), 7.1 (s, 10H, Ar-H)

EXAMPLE 8

7-Amino-3-exomethylene-3-cepham-4-carboxylic acid diphenyl methyl ester hydrochloride To a solution of 7-phenoxy acetamido-3-exomethylene-3-cepham-1-oxide-4-carboxylic acid diphenylmethyl ester (20 g, 0.038 mole) in chloroform (300 mL) were added dimethyl dichlorosilane (19.6 g, 0.152 mole) and N,N-dimethyl aniline (18.41 g, 0.152 mole) at 15°-20° C. The reaction mixture was stirred for 1 hr. and cooled to −35° C. $PCl_5$(31.7 g, 0.152 mole) was added and the reaction mixture was further stirred for 2 hrs. at −30° C. The mixture was cooled to −50° C. and methanol (150 mL) was added. The solution was stirred for 1 hr. at −15° C. and 1 hr. at 15° C. Water (40 mL) was added and the mixture was concentrated under vacuum to remove methylene chloride and methanol. The solid thus obtained was filterd and dried. Yield 10.5 g (66.8%).

EXAMPLE 9

7-Amino-3-exomethylene-3-cepham-4-carboxylic acid diphenyl methyl ester hydrochloride To a solution of 7-phenyl acetamido-3-exomethylene-3-cepham-1-oxide-4-carboxylic acid diphenylmethyl ester (10 g, 0.019 mole) in methylene chloride (100 mL) were added pyridine (6.15 g, 0.077 mole) and cyclohexene (3.2 g, 0.038 mole) at 20° C. The reaction mixtgure was cooled to −40° C. $PCl_5$(16.5 g, 0.077 mole) was added and the reaction mixture was stirred for 45 minutes at −30° C. and 1.5 hrs. at 0° C. The mixture was cooled to −50° C. and methanol (62.3 g, 1.9 mole) was added. The solution was stirred for 1 hr. at −15° C. Water (10 mL) was added and concentrated under vacuum to remove methylene chloride and methanol. The semi-solid thus obtained was triturated with ether to give a white solid, which was filtered and dried. Yield 5.6 g (70%).

While the invention has been described by reference to specific examples, this was for purposes of illustration only. Numerous alternative embodiments will be apparent to those skilled in the art.

We claim:

1. A process for preparing 7-amino-3-exomethylene-3-cepham-4-carboxylic acid ester of the formula:

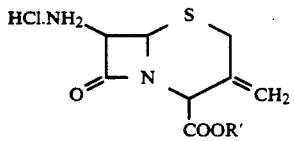

wherein R' is linear or branched chain alkyl, aryl, aralkyl, aryloxyalkyl, or alkoxyalkyl, comprising (a) reacting 7-acylamino-3-exomethylene-3-cepham-1-oxide-4-carboxylic acid ester of the formula:

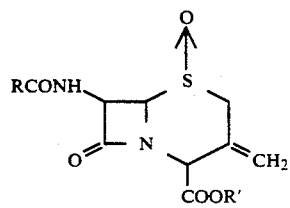

wherein R' is as defined above and R is aryl, aralkyl, or aryloxyalkyl, with a silylating reagent in an inert solvent and in the presence of a base to form an O-silyl derivative at the amido group, (b) adding an iminohalide forming agent to the reaction mixture to form an iminohalide intermediate, and (c) deoxygenating and deacylating said iminohalide intermediate by adding anhydrous alcohol to the reaction mixture.

2. The process of claim 1 wherein step (a) is carried out at a temperature of about 0° to about 50° C.

3. The process of claim 1 wherein step (a) is carried out at a temperature of about 10° to about 20° C.

4. The process of claim 1 wherein step (b) is carried out at a temperature of about −50° C. to about +20° C.

5. The process of claim 1 wherein step (b) is carried out at a temperature of about −30° C. to about −20° C.

6. The process of claim 1 wherein step (c) is carried out at a temperature of about −50° C. to about +30° C.

7. The process of claim 1 wherein step (c) is carried out at a temperature of about −30° C. to about +20° C.

8. The process of claim 1 wherein said iminohalide forming agent is a phosphorous halide.

9. The process of claim 1 wherein said iminohalide forming agent is phosphorous pentachloride, phosphorous pentabromide, phosphorous trichloride, or phosphorous tribromide.

10. The process of claim 1 wherein said anhydrous alcohol is methanol, ethanol, n-propanol, n-butanol, isobutanol, n-amyl alcohol, isoamyl alcohol, ethylene glycol, propylene glycol, or 1,3-propanediol.

11. The process of claim 1 wherein said base is a nitrogen-containing organic base.

12. The process of claim 1 wherein said base is triethyl amine, trimethyl amine, diethyl amine, dimethyl amine, pyridine, picoline, quinoline, N-methylmorpholine, N,N-dimethyl aniline, N,N-diethyl aniline, or lutidine.

13. The process of claim 1 where said inert solvent is methylene chloride, ethylene chloride, chloroform, carbon tetrachloride, or trichloroethane.

14. The process of claim 1 wherein said silylating agent is trimethyl chlorosilane, dimethyl dichlorosilane, methyltrichlorosilane, triethylchlorosilane, trimethylbromosilane, methoxytrichlorosilane, N,O-bistrimethyl silylacetamide.

15. A process for preparing 7-(D-phenylglycylamido)-3-chloro-3-cephem-4-carboxylic acid comprising preparing 7-amino-3-exomethylene-3-cepham-4-carboxylic acid ester as set forth in claim 1, converting said 3-exomethylene-3-cepham functionality to 3-chloro-3-cepham functionality, removing said R' ester group, and replacing said 7-amino group with a 7-D-phenylglycylamido group.

16. A process for preparing 7-amino-3-exomethylene-3-cepham-4-carboxylic acid p-nitrobenzyl ester hydrochloride of the formula:

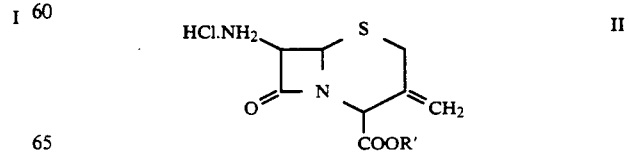

wherein R' is p-nitrobenzyl or diphenylmethyl, comprising (a) reacting 7-acylamino-3-exomethylene-3-cepham-1-oxide-4 carboxylic acid p-nitrobenzyl ester of the formula:

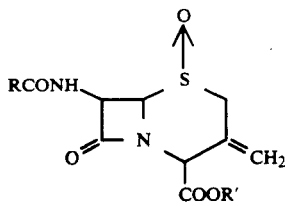

wherein R' is as defined above and R is aryl, aralkyl, or aryloxyalkyl, with a halogenated silylating agent in an inert solvent in the presence of a base to from an O-silyl derivative at the amido group;

(b) adding a phosphorous halide to the reaction mixture to form an iminohalide intermediate; and (c) simultaneously deoxygenating and deacylating said iminohalide intermediate by reacting said iminohalide intermediate with an anhydrous alcohol.

17. The process of claim 16 wherein said halogenated silylating agent is trimethylchlorosilane.

18. The process of claim 17 wherein said phosphorous halide is phosphorous pentachloride.

19. The process of claim 18 wherein said base is N,N-dimethylaniline.

20. The process of claim 19 wherein said alcohol is isobutanol, methanol, or 1,3-propanediol.

21. A process for preparing 7-amino-3-exomethylene-3-cepham-4-carboxylic acid ester of the formula:

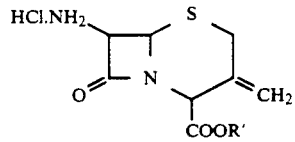

wherein R' is p-nitrobenzyl, p-methyoxybenzyl, benzhydryl, or diphenylmethyl, comprising a) reacting 7-acylamino-3-exomethylene-3-cepham-1-oxide-4-carboxylic acid ester of the formula:

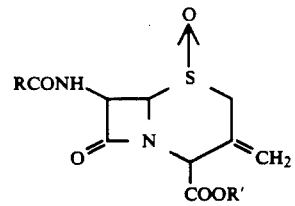

wherein R' is as defined above and R is benzyl, phenoxyethyl, phenoxy, phenyl, phenyl lower alkyl, or phenoxy lower alkyl, with a halogenated silylating agent in an inert solvent in the presence of a base;

b) adding an iminohalide forming agent to the reaction mixture to form an iminohalide intermediate; and c) simultaneously deoxygenating and deacylating said iminohalide intermediate by reacting said iminohalide with an anhydrous alcohol.

22. The process of claim 21 wherein said iminohalide forming agent is a phosphorous halide.

23. The process of claim 21 wherein said silylating agent is a halogenated silylating agent.

24. The process of claim 21 wherein said base is an organic base.

* * * * *